(12) United States Patent
Farrow et al.

(10) Patent No.: US 9,211,225 B2
(45) Date of Patent: Dec. 15, 2015

(54) LIMITED STRETCH COMPRESSION GARMENT APPARATUS AND METHOD

(71) Applicants: Wade P. Farrow, College Station, TX (US); Barry L. Creighton, College Station, TX (US)

(72) Inventors: Wade P. Farrow, College Station, TX (US); Barry L. Creighton, College Station, TX (US)

(73) Assignee: FARROW INNOVATIONS LLC, Bryan, TX (US)

( * ) Notice: Subject to any disclaimer, the term of this patent is extended or adjusted under 35 U.S.C. 154(b) by 50 days.

(21) Appl. No.: 14/194,617

(22) Filed: Feb. 28, 2014

(65) Prior Publication Data

US 2014/0180183 A1    Jun. 26, 2014

Related U.S. Application Data

(63) Continuation of application No. 10/975,590, filed on Oct. 28, 2004, now Pat. No. 8,663,144.

(60) Provisional application No. 60/555,150, filed on Mar. 22, 2004.

(51) Int. Cl.
  *A61L 15/00*  (2006.01)
  *A61H 1/00*   (2006.01)
  *A61F 13/08*  (2006.01)

(52) U.S. Cl.
  CPC .............. *A61H 1/008* (2013.01); *A61F 13/085* (2013.01)

(58) Field of Classification Search
  CPC ................... A61F 13/49011; A61F 13/49015; A61F 13/5622; A61F 13/49017; A61F 13/15203; A61F 13/505; A61F 13/5633; A61F 13/49004; A61F 13/49012; A61F 13/55115; A61F 13/84; A61F 2013/49493; A61F 2002/5055; A61F 2/7812; A61F 2002/30065; A61F 2002/30069; A61F 2002/3021; A61F 2002/30324; A61F 2002/5007; A61F 2002/7818; A61F 2210/0071; A61F 2230/0067; A61F 2250/0036; A61F 13/06; A61F 13/14; A61F 2005/0179; A61F 5/0102; A61F 5/0106; A61F 5/026; A61F 13/066; A61F 13/108; A61F 5/0111; A61F 5/0118; A41D 13/0015; A61H 39/04; A63B 21/0004; A63B 21/05
  USPC ........... 602/20–28, 60–62; 128/878–879, 888
  See application file for complete search history.

(56) References Cited

U.S. PATENT DOCUMENTS 2,687,723 A    8/1954  Stern
2,816,361 A   12/1957  Jobst (Continued)

FOREIGN PATENT DOCUMENTS

| GB | 2373444        | 9/2002  |
|----|----------------|---------|
| WO | WO 99/36019    | 7/1999  |
| WO | WO 00/15139    | 3/2000  |
| WO | WO 2005/092401 | 10/2005 |
| WO | WO 2008/127929 | 10/2008 |

OTHER PUBLICATIONS

3M Coban 2 Layer Compression System, Commonly Asked Questions, Feb. 13, 2007, pp. 1-3.

(Continued)

*Primary Examiner* — Michael Brown
(74) *Attorney, Agent, or Firm* — Shumaker, Loop & Kendrick, LLP

(57) ABSTRACT

An apparatus for applying pressure to a body part comprising multiple interconnectable bands of compressible or noncompressible material. Optional spine to further interconnect the bands. Interconnectable pieces designed for covering specific body areas. Modular arrangement of the individual components. Customized or off-the-shelf availability of the apparatus.

33 Claims, 5 Drawing Sheets

(56) References Cited

U.S. PATENT DOCUMENTS

| | | | |
|---|---|---|---|
| 3,298,366 A | | 1/1967 | Moore et al. |
| 3,312,219 A | | 4/1967 | Peckham |
| 3,699,959 A | * | 10/1972 | Garrahan et al. ............... 602/65 |
| 3,856,008 A | | 12/1974 | Fowler |
| 4,172,456 A | | 10/1979 | Zens |
| 4,215,687 A | * | 8/1980 | Shaw ............................. 602/60 |
| 4,502,301 A | | 3/1985 | Swallow et al. |
| 4,577,622 A | | 3/1986 | Jennings |
| 4,756,026 A | | 7/1988 | Pierce, Jr. |
| 4,926,846 A | * | 5/1990 | Nassar ........................... 602/27 |
| 4,971,044 A | | 11/1990 | Dye |
| 5,036,838 A | * | 8/1991 | Sherman ........................ 602/44 |
| 5,218,954 A | | 6/1993 | van Bremmelen |
| 5,387,183 A | | 2/1995 | Jones |
| 5,520,630 A | | 5/1996 | Daneshvar |
| 5,546,955 A | | 8/1996 | Wilk |
| 5,617,745 A | | 4/1997 | Della Corte et al. |
| 5,653,244 A | | 8/1997 | Shaw |
| 5,729,836 A | | 3/1998 | Ewing |
| 5,733,321 A | | 3/1998 | Brink |
| 5,741,220 A | | 4/1998 | Brink |
| 5,897,518 A | | 4/1999 | Shaw |
| 5,906,206 A | | 5/1999 | Shaw et al. |
| 5,918,602 A | | 7/1999 | Shaw et al. |
| 5,993,405 A | | 11/1999 | Wynn |
| 6,109,267 A | | 8/2000 | Shaw et al. |
| 6,123,681 A | | 9/2000 | Brown, III |
| 6,152,893 A | | 11/2000 | Pigg et al. |
| 6,254,554 B1 | | 7/2001 | Turtzo |
| 6,283,124 B1 | | 9/2001 | Schleuning et al. |
| 6,338,723 B1 | | 1/2002 | Carpenter et al. |
| 6,415,525 B1 | | 7/2002 | Watkins |
| 6,536,051 B1 | | 3/2003 | Oh |
| 6,573,419 B2 | | 6/2003 | Naimer |
| 6,613,007 B1 | | 9/2003 | Reid, Jr. |
| 6,617,485 B2 | | 9/2003 | Herzberg |
| 6,805,681 B2 | | 10/2004 | Yokoyama |
| 6,852,089 B2 | | 2/2005 | Kloecker et al. |
| 6,860,862 B2 | | 3/2005 | Waldridge et al. |
| 7,135,007 B2 | | 11/2006 | Scott et al. |
| 7,173,161 B1 | | 2/2007 | Kandt |
| 7,329,232 B2 | | 2/2008 | Lipshaw et al. |
| 7,513,881 B1 | | 4/2009 | Grim et al. |
| 7,867,185 B2 | | 1/2011 | Lipshaw |
| 7,942,838 B2 | | 5/2011 | Farrow |
| 8,221,340 B2 | | 7/2012 | Farrow |
| 8,251,933 B2 | | 8/2012 | Farrow |
| 8,376,977 B2 | | 2/2013 | Farrow |
| 8,491,514 B2 | | 7/2013 | Farrow |
| 8,529,483 B2 | | 9/2013 | Farrow |
| 8,663,144 B2 | | 3/2014 | Farrow et al. |
| 8,747,341 B2 | | 6/2014 | Farrow et al. |
| 8,808,210 B2 | | 8/2014 | Farrow |
| 2002/0022791 A1 | | 2/2002 | Morris et al. |
| 2003/0149389 A1 | | 8/2003 | Daneshvar |
| 2004/0122344 A1 | | 6/2004 | Nelson et al. |
| 2005/0113729 A1 | | 5/2005 | Scott et al. |
| 2005/0192524 A1 | | 9/2005 | Lipshaw et al. |
| 2005/0209545 A1 | | 9/2005 | Farrow |
| 2006/0010574 A1 | | 1/2006 | Linnane |
| 2007/0276310 A1 | | 11/2007 | Lipshaw et al. |
| 2007/0282232 A1 | | 12/2007 | Hoffman |
| 2010/0056973 A1 | | 3/2010 | Farrow et al. |
| 2011/0125183 A1 | | 5/2011 | Lipshaw et al. |
| 2012/0179084 A1 | | 7/2012 | Lipshaw et al. |

OTHER PUBLICATIONS

3M Coban 2 Layer Compression System, Patient Instructions, 2006, 1 page.

New 3M Coban 2 Layer Compression System Introduced for the Treatment of Edema Associated with Venous Leg Ulcers, Press Release, May 1, 2006, pp. 1-3.

Farbifoam Achilles Healer, http://www.fabrifoam.com/p-achilleshealer.html, retrieved Sep. 30, 2005.

Fabrifoam AnkleGard, http://www.fabrifoam.com/p-anklegard.html, retrieved Sep. 30, 2005.

Fabrifoam AnkleWrap, http://www.fabrifoam.com/p-anklewrap.html, retrieved Sep. 30, 2005.

Fabrifoam CarpalGard, http://www.fabrifoam.com/p-carpalgard.html, retrieved Jan. 7, 2010.

Fabrifoam ElbowGard, http://www.fabrifoam.com/p-elbowgard.html, retrieved Jan. 7, 2010.

Fabrifoam KneeGard, http://www.fabrifoam.com/p-kneegard.html, retrieved Sep. 30, 2005.

Fabrifoam MediWrap, http://www.fabrifoam.com/p-mediwrap.html, retrieved Jan. 7, 2010.

Fabrifoam NustimWrap, http://www.fabrifoam.com/p-nustimwrap.html, retrieived Sep. 30, 2005.

Fabrifoam PattStrap, http://www.fabrifoam.com/p-pattstrap.html, retrieved Jan. 7, 2010.

Fabrifoam ProWrap, http://www.fabrifoam.com/p-prowrap.html, retrieved Sep. 30, 2005.

Fabrifoam PSC, http://www.fabrifoam.com/p-psc.html, retrieved Sep. 30, 2005.

Fabrifoam SuperWrap, http://www.fabrifoam.com/p-superwrap.html, retrieved Sep. 30, 2005.

Fabrifoam WristWrap, http://www.fabrifoam.com/p-wristwrap.html, retrieved Jan. 7, 2010.

ASICS Men's Shooting Sleeve, www.amazon.com/exec/obdios/ASIN/B000J40NYU/nextag-sg-20/ref-nosim, printed Feb. 1, 2007, 4 pages.

NBA Shooting Arm Sleeve, www.jumpusa.com/nba.sub.--shooting.sub.--sleeves.html, printed Feb. 1, 2007, 2 pages.

Hawkins, A New Cohesive Short-Stretch Bandage and Its Application, British Journal of Nursing, Feb. 22, 2001-Mar. 7, 2001, pp. 249-253.

Lawrance, Use of Velcro Wrap System in the Management of Lower Limb Lymphoedema/Chronic Oedema, Journal of Lymphoedema, 2008, vol. 3, No. 2, pp. 65-70.

Mayrovitz, Compression Therapy: A Summary of Important Concepts and Features, 2004, pp. 1-11.

Medassist Orthotic Products, www.medassistgp.com, 6 pages.

Mosti et al., Compression Therapy in the Treatment of Leg Ulcers, Acia Vulnologica, vol. 7, No. 3, May 2009, pp. 1-20.

International Preliminary Examination Report completed Jul. 24, 2006 for PCT/US2005/09483, pp. 1-7.

International Search Report and Written Opinion of the International Searching Authority mailed Jul. 6, 2005 for PCT/US2005/09483, pp. 1-12.

Supplemental Partial European Search Report completed Mar. 19, 2008 for EP 05 73 1830, pp. 1-7.

International Search Report and Written Opinion of the International Searching Authority mailed Aug. 14, 2008 for PCT/US2008/059707, pp. 1-7.

Thomas et al., An Evaluation of a New Type of Compression Bandaging System, World Wide Wounds, Sep. 2003, pp. 1-15.

Trinity Lymphedema Centers, http://www.trinitylc.com/cmpgarm1.html, 3 pages.

Understanding Compression Therapy, Medical Education Partnership, LTD, 2003, pp. 1-17.

* cited by examiner

*Fig. 8*

Order Information

| Patient Last Name: | | First Name: | |
|---|---|---|---|
| Birth Date: | Sex: M / F | Height: | Weight: |
| Shoe size: | Foot piece type: Anklet / Leg Wrap | | |
| Leg: Right / Left / Both | | | |

202 → (table above)

200 ↙

Shipping Information

| Contact Person: | Company: | |
|---|---|---|
| Address: | | |
| City: | State: | Zip code: |
| Phone Number: | E-mail: | |

204 → (table above)

Billing Information

206 → Method of Payment: Check / Money Order / Credit Card / Insurance

Device Price:

| Left Leg |
|---|
| 1. Smallest Ankle Circumference (SAC): |
| 2. Circumference 2: |
| 3. Circumference 3: |
| 4. Circumference 4: |
| 5. Circumference 5: |
| 6. Knee crease to SAC: |
| 7. Heel to 5th met head: |
| 8. Midfoot circumference: |
| |
| Right Leg |
| 1. Smallest Ankle Circumference (SAC): |
| 2. Circumference 2: |
| 3. Circumference 3: |
| 4. Circumference 4: |
| 5. Circumference 5: |
| 6. Knee crease to SAC: |
| 7. Heel to 5th met head: |
| 8. Midfoot circumference: |

208 → (table above)

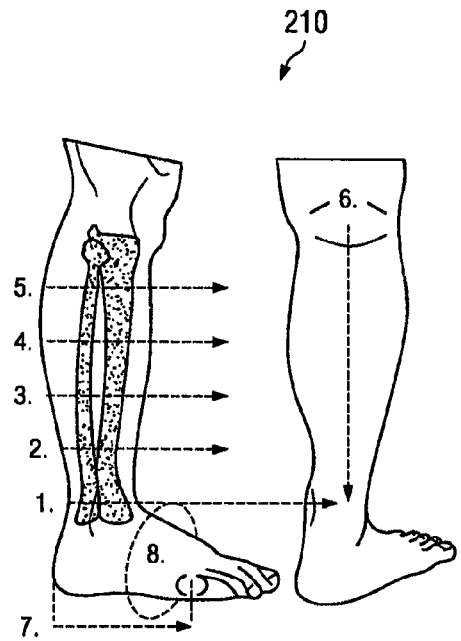

210

LIMITED STRETCH COMPRESSION GARMENT APPARATUS AND METHOD

RELATED APPLICATIONS

This application is a continuation of U.S. patent application Ser. No. 10/975,590 filed Oct. 28, 2004 (now U.S. Pat. No. 8,663,144), which claims the benefit of U.S. Provisional Patent Application Ser. No. 60/555,150 filed Mar. 22, 2004.

U.S. patent application Ser. No. 10/975,590 and U.S. Provisional Patent Application Ser. No. 60/555,150 are both hereby incorporated by reference.

BACKGROUND

The Background Art

Excessive interstitial fluid accumulation, referred to as edema, may arise from a variety of illnesses and conditions, including venous valvular insufficiency, postphlebotic syndrome, and lymphedema. Control of this edema by reduction of interstitial fluids is important to increase PO2 delivery to tissues, relieve pain from swelling, and decrease risk of infection. Decreasing drainage of fluid from sores, skin breaks, and/or ulcerations promotes wound closure, prevents wound breakdown, and decreases risk of blood clot formation in veins.

Thus, it is desirable to have a customizable or off-the-shelf compressive device that can be readily available for application to a body part to prevent excessive fluid accumulation resulting from a variety of diseases and maladies.

BRIEF DESCRIPTION OF THE DRAWINGS

FIG. 8 is an illustration of an order form for ordering a customized compression garment.

DETAILED DESCRIPTION

Figures 1, 2:
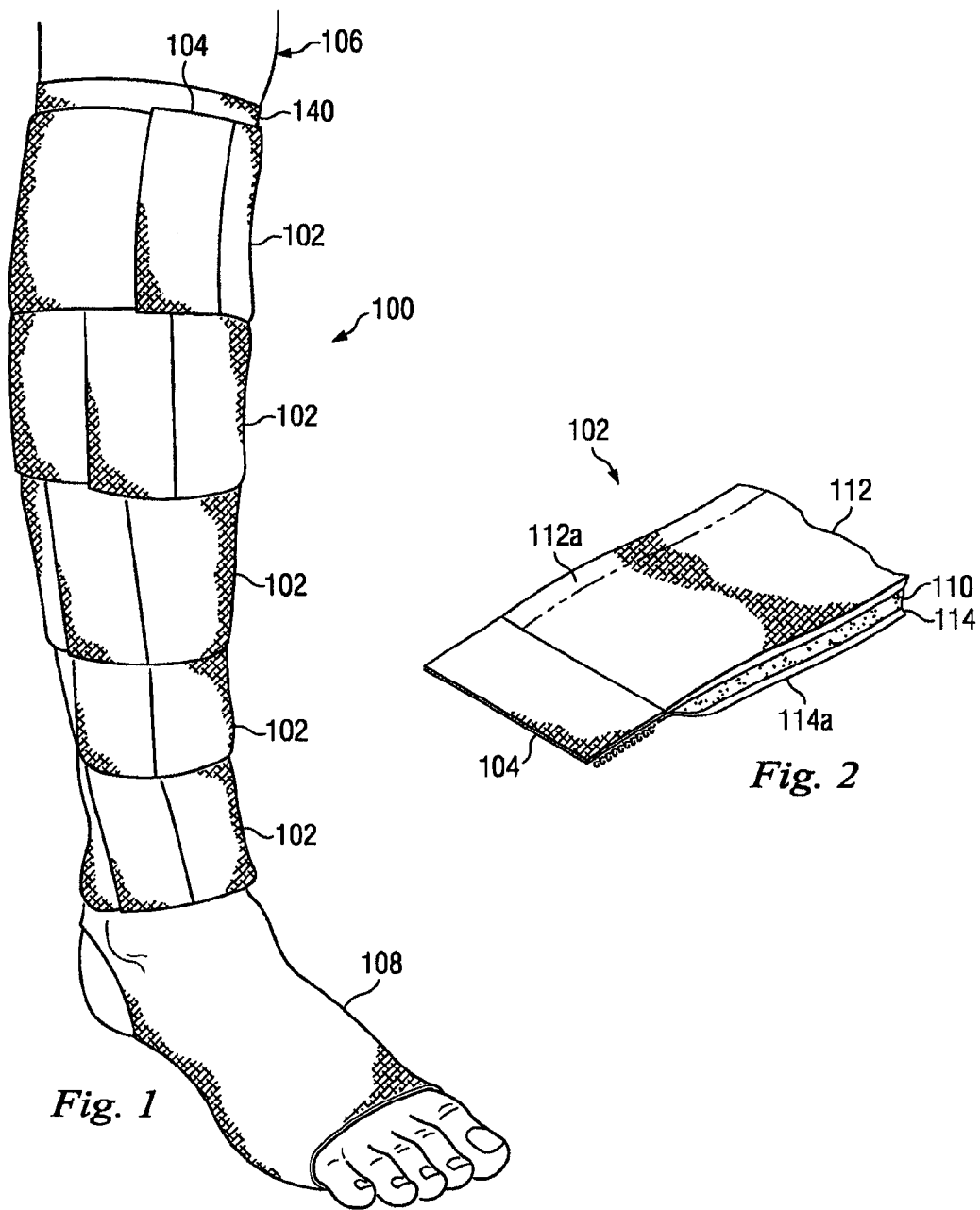
FIG. 1 is an illustration of one embodiment of a modular compression garment according to the present disclosure.
FIG. 2 is a perspective view of a band used in the modular compression garment of FIG. 1.

The present disclosure relates generally to treatment of edema and, more specifically, to a device for applying compressive pressure to a person's body in order to facilitate reduction of interstitial fluids from a body trunk and/or limb extremity and to provide support and fatigue relief.

It is to be understood that the present disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not, in itself, dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1 illustrates one embodiment of the present disclosure applied as a lower limb compression garment 100. In this embodiment, the lower limb compression garment 100 includes several bands 102 that are of adjustable size by way of attachment mechanisms 104 for conforming, in the present embodiment, to a human leg 106. The lower limb compression garment 100 also includes an anklet 108 for conforming to a human ankle.

It is understood that the present invention is not limited to use with the leg, but can be used in various limbs and trunks of humans. It is further understood the invention is not limited to humans, but may apply for veterinarian use such as for a horse, dog, or other animal. For example, another embodiment may be used to compress an entire leg or arm of a human or a leg of a horse or dog. Various embodiments of the present disclosure may also provide for maximal access to a portion of a limb. These embodiments may have the compression band 102 over the affected area on top, with the proximal and distal compression bands underlapping. This may allow removal of a compression band or bands 102 over the affected area, while not requiring removal of the entire garment. Thus, the rest of the garment 100 may remain therapeutic while the area is accessed.

1. The Bands 102 and Attachment Mechanisms 104

Referring also to FIG. 2, the bands 102 may include an inner layer 114 and an outer layer 112 with optional elastomeric compression material layer 110. In one embodiment an elastomeric loop material 112 such as Shelby Elastics Mon-3 or WonderWrap (Shelby, N.C.) may be sewn onto a backing of elastomeric fabric 114 such as Schoeller® Prestige 58012 (Sevelen, Switzerland). The elastomeric fabric 114 may be sewn on-the-bias so as to provide more stretch. For higher compression for a given amount of stretch, the fabric 114 may be sewn not-on-the-bias. Therefore sewing a highly elastic loop fabric 114 onto the backing of the material 110 may alternate percentage stretchability and alternate the compression gradient, based upon material selection and if it is sewn on-the-bias or not on-the-bias. Sewing such elastomeric fibers 114 on-the-bias may allow more stretch but less compression. For example, sewing the WonderWrap on the Schoeller fiber on-the-bias may result in a 20-30% elastomeric range with good compression. Sewing the Wonder-Wrap on the Schoeller fiber not on-the-bias may result in a 15-20% elastomeric range with more compression. This way several embodiments can be easily engineered to provide different common classes of compression such as 8-15 mm, 15-20 mm, 20-30 mm, 30-40 mm, or 40+mm. This may allow the garment 100 to be applied lightly or tighter and more therapeutic. If applied past the range of the therapeutic stretch, then the compression applied may be directly proportional to that the user applies.

In other embodiments, a thin semi-compressible layer 110 is provided between an inner layer 114 and the outer layer 112 of the bands 102. This layer 110 may be made of polyurethane foam such as Rosidal Soft (Lohmann Rauscher Neuwied, Germany). Such foam would ideally by 0.3 cm thick, although other ranges of thickness 0.05 cm to 5 cm are possible. The layer 110 may include particles made of compressible, high resiliency, low density, open cell plastic foam. Such particles ground up and of different particle sizes and shaped particles can create areas of high pressure areas and intersecting networks of low pressure areas at the seams. Use of such particles for compression garments is known in the art and sold as the Tribute™ (Solaris Inc. Brookfield, Wis.). Other materials for the compressible layer 110 may include rubber, plastic air bubbles, foam air bubbles, or non-convolute foam. The semi-compressible layer 110 may have channels sewn in them to create lines of natural lymph flow or criss-cross pattern. Alternatively, in other embodiments the foam may serve as the inner layer with a loop-compatible fabric or elastomeric material as the outer layer.

In still other embodiments, the bands 102 may not be multi-layered, as described above, but consist essentially of elastomeric yarns, for example, PowerNet™ nylon or nylon/spandex, ComfortWeave™ polyester/spandex, Clearspan® spandex manufactured by Radici, Dorlastain® spandex manufactured by Bayer, Lycra® spandex manufactured by DuPont, and any other spandex yarn, or special woven cotton fabrics such as Comprilan® short-stretch bandage, manufactured by Beiersdorf AG. Another elastomeric compression material that may be used is Lovetex® Industrial Corporation Breathe Freely (Taipei, Taiwan). It is understood in the spirit of the disclosure that any suitable elastic material may be used and is not limited to those listed above. In the present example, the chosen material would be in a range of 15% to 100% elastic stretch, although other ranges are anticipated.

In still other embodiments, the band 102 may include the elastomeric semi-compressible layer and a thin outer layer of Velcro® (hook and loop) compatible fabric. Such a garment may be sold as a reusable, semi-disposable, or disposable garment. For example, as single-use embodiment might be sold sterile and for application directly after surgery on an affected limb in order to control swelling and prevent wound dehiscence, or to allow selective access postoperatively to access directly over incision or wound, while leaving rest of garment in tact. Other single-uses may include general hospital use or as outpatient clinic or home use in order to reduce or control interstitial edema. Alternative uses may be to hold a bandage or medication against a limb member.

The attachment mechanisms 104, which is connected to or connectable to the bands 102, allow the bands to interconnect to one another. The attachment mechanisms 104 can be of various types such as hooks, snaps, buttons, and glue/adhesive, and some mechanisms for some bands 102 may be different than those for other bands on the same garment 100. In the example of FIG. 2, the attachment mechanisms include a hook-and-loop fastener, such as a Velcro® strip. Each band 102 may fasten to itself in such a way as the user can apply the band under compression and it will hold the compression against the body part. The hook of the hook-and-loop fastener may be sewn onto one end of the band and the body of the band or a portion thereof may have the loop material.

In this embodiment, some or all of the exterior surfaces 112 of the bands 102 may include elastomeric loop material. The material therefore may interlock with the hook material of the attachment mechanisms 104 and/or a spine (discussed below). The use of loop material along the outside layer 112 of the band 102 allows each band to apply to a wider range of compression. Also, the use of elastomeric loop material may allow the dual function of attachment to the other end of the band, which has hook material, as well providing active compression.

In varying embodiments, the bands 102 interconnect to each other in a temporary, semi-permanent, or permanent manner. The connections may use chemical, thermal, or mechanical bonds. Mechanical temporary and semi-permanent bonds may include hook and loop, snaps, button and button-holes, or ties and eyelets. Mechanically bonded permanent attachments may include methods such as sewing and stapling. Chemical bonding includes methods such as fabric glue and super glue. Such glue is well-known in the art and used extensively in the industry for upholstery, furniture, and other products. Other forms of chemical bonding include tape adhesive such as PEELnSTICK and the acid-free acrylic double-sided adhesive SuperTape (Therm O Web, Wheeling Il). Thermal bonding may include iron-on interfacing, ultrasonic welding of compatible components, or thermal melting of compatible components or iron-on interfacing. Such iron-on interfacing may for example include one or more layers of HEATNBOND® Ultrahold (Them O Web, Wheeling Il). Some of the bonds (e.g., hook and loop) allow the garment 100 to be reused many times. Other bonds (e.g., fabric glue) may allow the garment 100 to be reused only a certain number of times. For example, the fabric glue may be reusable for a period of days, but afterwards may loose its adhesion properties. Still other bonds (e.g., thermal welding) are for a single use.

For example, a lower perimeter 114a (towards the foot in the present embodiment) of the interior layer 114 may include a relatively soft hook material. The soft hook material 114a may overlap on the band 102 immediately below, thus interlocking between the adjacent bands and providing additional stability of the device. Alternatively, an upper perimeter 112a (away from the foot in the present embodiment) of the outer layer 112 may include hook material. The lowest band may attach to loop material sewn onto the anklet 108 or attach to the elastomeric loop band at the top of the footpiece. In some embodiments, there will be no soft hook material at the facing edges of the bands and the bands will simply overlap each other with the lowest band overlapping an anklet or footpiece.

Small geographic symbols may be drawn or printed on each band 102 which will change shape in a characteristic way when the proper compression is applied so that the user knows the prescribed therapeutic compression is being applied. Such symbols are well known in the art, and are applied currently to short-stretch bandages such as sold by SSL International PLC under the trade name of Setopress (London, England). In another embodiment, material color or material markings will differentiate different bands of varying levels of compression.

2. The Spine 120

Figure 3:
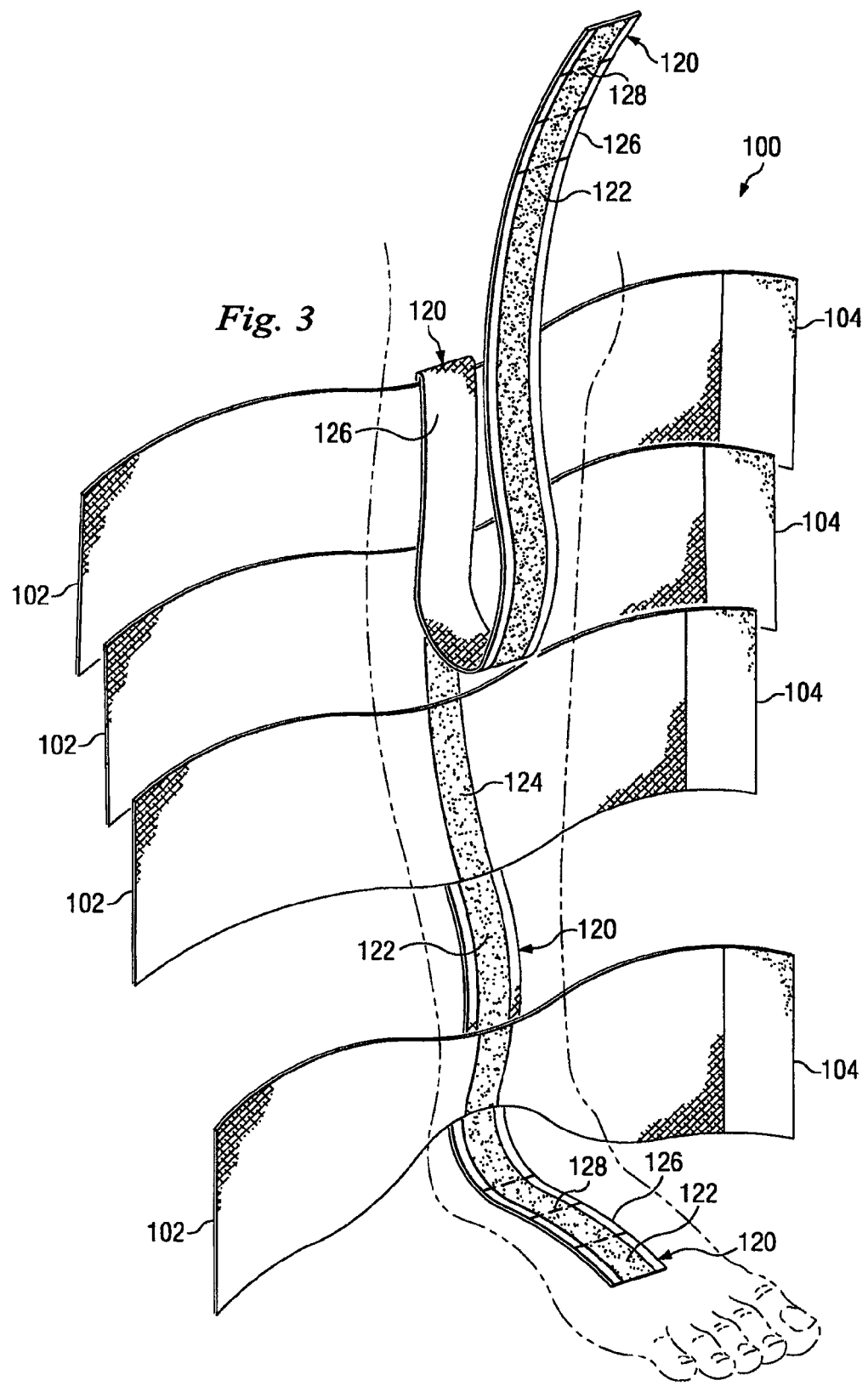
FIG. 3 is a break-away view of the compression garment of FIG. 1 including one embodiment of a spine used for connecting a plurality of bands such as those shown in FIG. 2.

Referring now to FIG. 3, in one embodiment, the bands 102 are joined together at a spine 120. The bands 102 can be joined to the spine 120 in various manners, and in the present embodiment they are sewn together. The spine 120 may comprise non-elastic or elastic material. There may be no difference in bulk or therapeutic application of this embodiment. Furthermore, the bands 102 may be partially or completely sewn together. In this embodiment, the bands 102 and spine 120 may be separately pre-manufactured, and then sewn together once measurements are made of the affected limb. By modifying the degree of overlap of the bands and the number of bands, a wide geometry of limbs may be fitted. The anklet 108 (FIG. 1) may be sewn to either or both of the spine 120 and the adjacent band 102.

In the embodiment of FIG. 3, the spine 120 extends both on an inside (adjacent the leg) and outside (external) of the lower limb compression garment 100. In furtherance of the example, the spine 120 includes hook material 122 for engaging with loop material 124 on the bands 102 (the loop material can be on both the inside and outside portions of the bands). An outer layer 126 is also provided, which may be either relatively stiff or rigid, which can facilitate the assembly and fitting of the lower limb compression garment 100, or may have elasticity which can facilitate the movement of the lower limb compression garment once in place.

Other embodiments may use one spine, one on the inside or one on the outside. Other embodiments may forego the spine as the hook-and-loop fastener or other connective means lengthwise centrally in each band 102 and overlapping may provide adequate connection to hold the device together as a single unit for application or storage.

In some embodiments, the spine 120 may also serve to connect the anklet 108 (FIG. 1). In other embodiments, the bands 102, spine 120, and/or anklet 108 can be attached using other mechanisms, such as glue or adhesive, snaps, or buttons. Furthermore, the spine 120 can be sewn or otherwise segregated into increments 128 so that it can easily be cut or shortened, as needed. For a lower limb, the spine may be 12, 13, 14, or 15 inches in length with increments, although single lengths of spine for different uses are within the scope of the present disclosure. For use as an upper limb compression device, for example, the spine may preferentially go the entire length of the arm along the outside edge. This may necessitate a longer spine and such permeations are within the scope of the present disclosure. Additionally, the spine may wrap around from one side to the other to allow for attachment of excess length or for additional stability of the device. Additionally, it is understood that other modular configurations exist within the scope of the present disclosure, such as any other attachment of the spine to the compression bands or method of attachment of one band to another. These may include buttons, snaps, zippers, or other methods of attachment.

Figure 4:
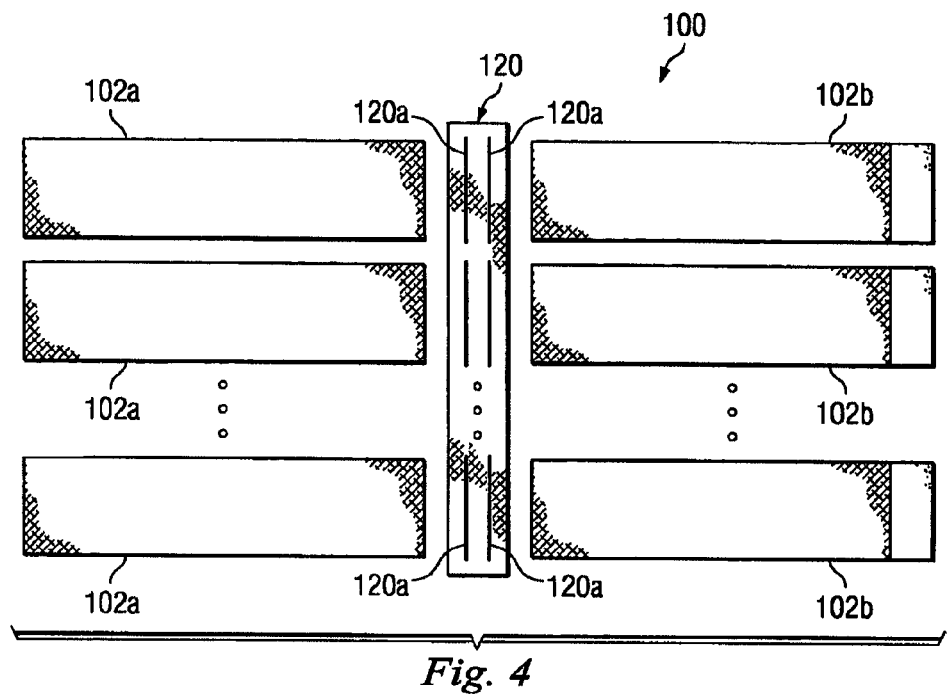
FIGS. 4 and 5 are alternative embodiments of a modular compression garments of the present invention.

Referring now to FIG. 4, in another embodiment, there are two bands, designated 102a, 102b, for each band "level." These bands 102a, 102b interconnect to each other and/or the spine 120. The spine may include slits 120a to assist in interconnection of the garment 100. The interconnectivity of the spine 120 to the bands 102a, 102b may be any method of mechanical, chemical, or thermal. In yet another embodiment, a single band (102, FIG. 1) can be fed through the slits 120a to position each band on the spine 120.

Figure 5:
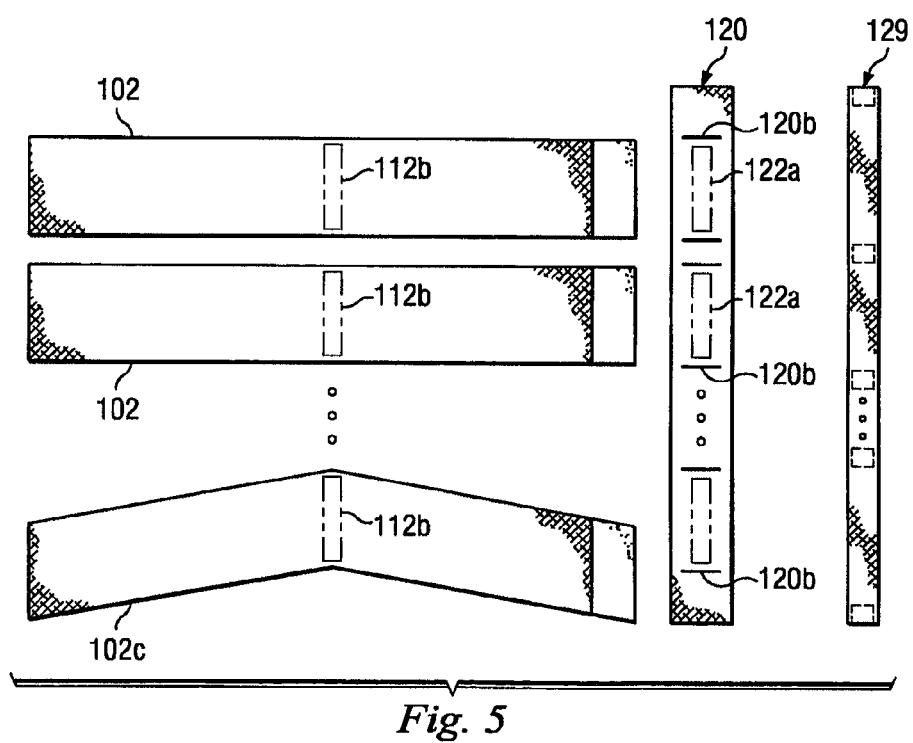

Referring to FIG. 5, in yet another embodiment, the spine 120 includes horizontal slits 120b and an optional cover member 129. The bands 102 fit against the spine 120 and may or may not attach at positions 122a for the spine and 112b for the band. The cover member 129 can then be weaved in and out of the slits 120b in order to hold the bands against the spine. The cover member 129 may attach just at the ends, or may attach at locations between each band 102. Again, any interconnections may be temporary or permanent and may include mechanical, chemical, or thermal bonds or a combination thereof.

Not all of the bands 102 need to be similarly constructed. For example, one of the bands in FIG. 5, designated with reference numeral 102c, is formed as a chevron, connecting with the spine 120 at the apex of the chevron. Such shape of a band may be desirable to create a more ergonomic angle on the limb. Such angles are preferably applied perpendicular to the skin, with more angle around the upper and lower curves of the calf than the rest of the garment. Such angles may vary according to limb geometry and garment size. Also, different bands can have different levels of elasticity. This would allow the garment 100 to be placed in different scenarios, such as over a bladder used for pneumatic pumps for preventing deep venous thrombosis. Also different levels of compression can be provided for bands 102 nearer the ankle (or wrist, or shoulder) than further away from the ankle. This selection of a specific elasticity can therapeutically treat edema or decreasing vein size to prevent blood clots.

Furthermore, bands 102 can have different amounts of compressions and expansion, either compared to each other or different amounts along the band itself. Using different levels of compression may be desirable for different garments. Further, graduated compression may be accomplished by using bands of various levels of compression in the same garment. For example, generally more compression may be desired in the ankle portion and less proximally for a leg compression garment. By using different band composition to vary the stretch, different levels of compression may be achieved. In another example, a band may have less stretch in the portions that intersect the spine 120, and more compression near the ends that are used for the locking mechanism 104. Thus, an assembled device can therapeutically apply varying levels of compression. When the user feels that the band no longer stretches, then the compression becomes different and proportional to the tension placed on the band. The user can thus learn to "dial in" to this difference and so more reliably and predictably apply the desired level of compression. By varying the length and width of a band and/or the composition of the band, any desired level of compression can be created in the band.

3. The Anklet 108

Referring again to FIG. 1, the anklet 108 can be configured as a sock or stocking, being relatively thin so that a shoe can be worn over the garment. In one embodiment, the anklet 108 is made of a synthetic stretch-fiber fabric such as a Lycra® brand material. In some embodiments the anklet 108 may or may not fasten to the rest of the garment 100. For example, a compression anklet can be used and placed in position with, but not attached to, the garment 100.

Figure 6:
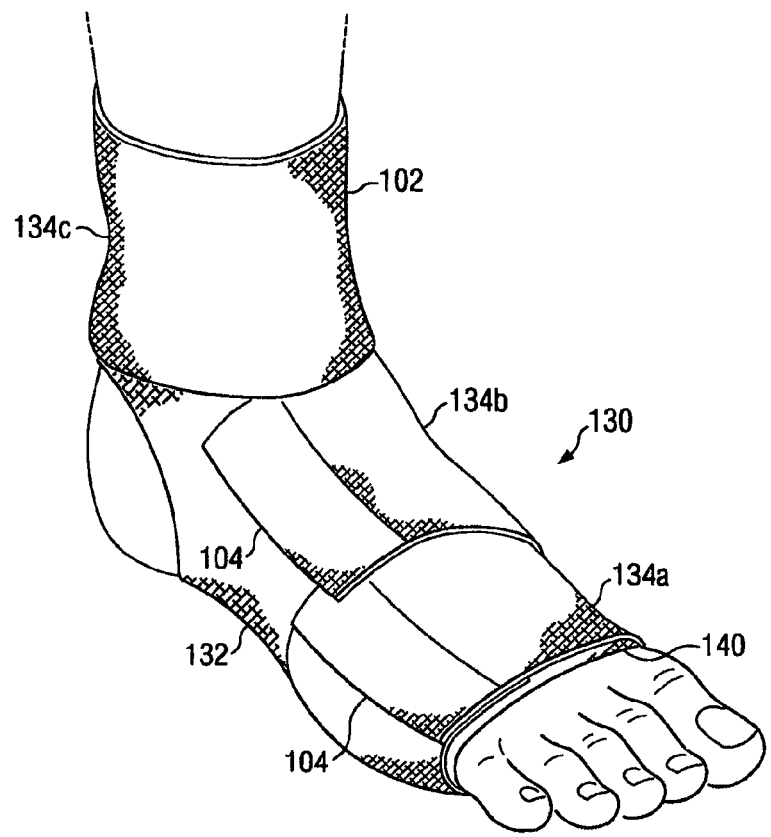
FIG. 6 is a side perspective view of a footpiece for use with a modular compression garment.

Referring now to FIG. 6, in another embodiment, a footpiece 130 can be used as a different kind of anklet. In one embodiment, the footpiece 130 includes an inner sock-like member 132 of cotton/Lycra blend and three outer bands 134a, 134b, 134c of elastomeric material. Other materials and construction can be chosen in order to alter the compression level of the device. Construction may be made of same materials and layers as in FIG. 2. In some embodiments, the material may be an elastic or non-elastic material and of one single layer or many overlapping layers.

The three elastomeric bands 134a, 134b, 134c are arranged so that the first elastomeric band 134a fastens over the forefoot, the second elastomeric band 134b is angled at approximately ninety degrees to the surface of the midfoot, and the third elastomeric band 134c is fastened parallel to the back of the Achilles. In the present embodiment, the third elastomeric band 134c is unique from the other two in that it can attach in place across, or across and downward onto the dorsum of the footpiece. Thus the design is unique in that it allows to fit a variety of foot sizes and to apply variable compression as desired to be most therapeutic.

The footpiece 130 also includes a single band 134c sewn in place in the middle with both free ends with sewn hook material. The hook material may be fastened circumferentially across just below the ankle, or may reach down toward the forefoot and across to the opposite side, for example. The flexibility of this band allows a number of geometries to be accounted for. In one embodiment, the band is just over three inches wide. The length of the band may be any desired length for therapeutic use. For example, lengths of 6 inches, 8 inches, 10 inches, 12 inches, 14 inches, 16 inches, and 18 inches, or other lengths are possible.

4. Stockings and Liners

Referring to FIGS. 1 and 6, a stocking liner 140 may be provided under the garment 100 to reduce itching and minimize effects of overlapping on the skin. The liner can extend the entire length of the garment 100, including any ankle 108 or foot piece 130, or may cover only a portion thereof. The liner 140 can be formed of a cotton/Lycra® blend or other material and may have a foam lining. The foam lining may include sewn channels to follow the body's natural lymphatic drainage lines. The foam lining also may have foam with stitches or carved portions to create a waffle-like pattern in order to facilitate lymphatic drainage in the un-compressed portions. The thickness of such a liner 140 may be quite thick, such as can be achieved with the JoviPak UE-P-AG1 (Tri-D Corporation Kent, Wash.). The foam may include a granular-type material. A fabric cover may also be included on all or part of the foam lining.

Figure 7:
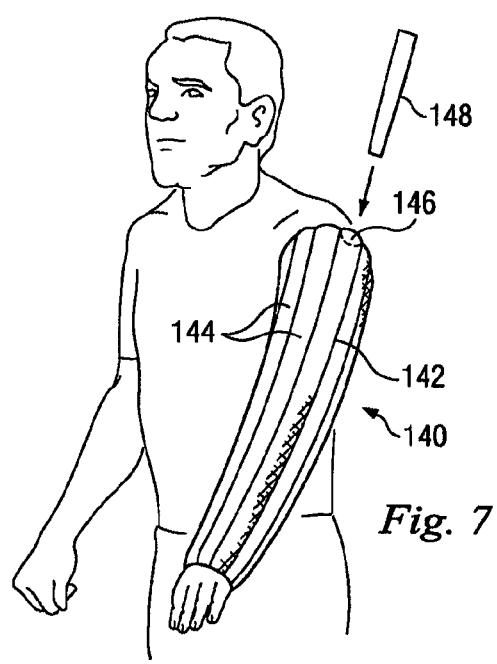
FIG. 7 is a side view of a liner for use with a modular compression garment.

Referring also to FIG. 7, the liner 140, shown here being used with an arm compression garment, would have a multiplicity of pressure-applying resilient protrusions, or high pressure areas 142 and channels 144 there between. The channels 144 potentially facilitate lymphatic drainage while reducing interstitial edema along the high pressure areas 142. The liner 140, which may be constructed similarly to commercial products known under the brand JoviPak, Tribute™ or Komprex II, may be a cotton or blended material with thicker woven fabric as seen in many commercially available socks.

Another embodiment of the liner 140 may include one or two layers of cotton or cotton/Lycra blend or another similar woven or formed material, with semi compressible material woven between the inner and out layers of the liner. The liner 140 may also include the channels 144 which are in the form of sewn pockets with openings 146 for insertion of a semi-compressible insert 148 to form the high pressure areas 142. Such an embodiment may have distinct advantages over other commercially available liners since it may be much thinner but with similar performance. This allows more comfort for long-term wear and improved breathability of the liner 140. The liner 140 may be designed for a specific use, but may have additional uses under other commercially available compression devices, such as The Cinch (Innovative Medical Solutions, Seattle Wash.), ReidSleeve (Peninsula Medical Inc., Scotts Valley Calif.), short-stretch or medium-stretch bandages, CircAid (San Diego Calif.) or other commercially used products for treatment of edema, venous and lymphedema. The insert 148 is preferentially thin and less than 1 cm, although larger sizes may also be desirable.

In another embodiment, foam padding can be positioned in-between the liner 140 and the straps 102. The foam padding can be used to reduce lymphedema. One possibility is to use dense foam such as Komprex foam (Lohmann Rauscher Neuwied, Germany). In this embodiment, the foam is cut into small squares of 0.25 cm to 2 cm along each side. These squares may or may not have a pyramid shape facing the inner layer. These pyramid-shaped areas massage the affected area during wear and can break up fibrotic areas, effectively reducing lymphedema long-term. Alternatively, one solid piece of foam with a grid but out on one side may achieve the same function. Other foam padding includes JoviPak Multi-Purpose pads (Tri-D Corporation Kent, Wash.) or other commercially available products such as the Jovi Le-C-Advi sheet foam liner. Such pads are sewn chips or pieces of polyurethane or similar foam and may or may not have channels sewn into place.

5. Business Method

Referring now to FIG. 8, the garments 100 discussed above can be provided in response to receiving a customer order form 200. The form 200 includes an order information section 202, a shipping information section 204, a billing information section 206, a measurement section 208, and a measurement guide 210. A customer can obtain and fill out the form 200 where measurements are taken of key components of the affected limb. If the place of assembly for the garment 100 is the same as the place of sale, then the measurements may be compared to pre-stocked components and the proper number and type of components can be selected. The modularity of the garment 100 facilitates a sales facility in having a reduced inventory yet still being able to provide a highly-customized solution.

Furthermore, the amount of overlap of bands may be varied to accommodate a variety of leg lengths. In one embodiment, the bands 102 are just over three inches in height, and each lower limb compression device may have 4-6 bands, one to two spines 120, and a footpiece or anklet 108. Since the spine 120 may be modular, one spine may accommodate an arm or a lower leg. Other spines, such as for an entire lower limb device, may also be provided. In another embodiment, the spine 120 may include a material backing with iron-on interfacing. This will allow quick permanent assembly of a plurality of bands 102 with or without an anklet. This customization can be done at the time of measurement of the actual limb, or can be done at a remote location using the measurement form 200.

In some embodiments, one or more of the bands 102 can be overlapped and connected (e.g. sewn together) prior to delivering to a doctor or patient. In other embodiments, some or all of the garment 100 can be sterilized prior to delivery.

Some embodiments of the form 200 can include information that would allow a doctor or provider to custom select certain bands 102 for different purposes. For example, different levels of edema (e.g., minimal, extreme) can be addressed by selecting an appropriate elasticity of the bands 102. Also, the height and/or weight of a patient can factor into the selection of band size, placement (e.g., more elastic bands near the ankle) and composition. The bands 102 can include a marker such as a position number that will indicate their placement on the spine 120.

The foregoing has outlined features of several embodiments according to aspects of the present invention. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of treatment comprising:
    selecting a patient suffering from venous insufficiency, postphlebitic syndrome, lymphedema, edma, painful swelling, or excessive fluid accumulation;
    obtaining a therapeutic compression garment comprising:
        a first band of material, the material comprising a first, elastomeric component, a second component distinct from the first component, and the first component connected to the second component such that the second component limits the stretch of the first component to define an end stretch of the material, and
        a first attachment mechanism connected to the first band;
    wrapping the first band around a limb of the patient;
    securing, by the first attachment mechanism after the wrapping, the first band wrapped around the limb; and
    delivering, by the therapeutic compression garment after the securing, therapeutic compression in the range of 8-15 mm Hg, 15-20 mm Hg, 20-30 mm Hg, 30-40 mmHg, or greater than 40 mm Hg to the limb.

2. The method of claim 1, wherein:
the first component comprises a first layer of the material; and
the second component comprises a second layer of the material.

3. The method of claim 2, wherein the material comprises a thin, semi-compressible layer positioned between the first layer and the second layer.

4. The method of claim 1, wherein:
the first component comprises elastomeric loop material forming a first layer of the material; and
the second component comprises a woven elastomeric fabric forming a second layer of the material.

5. The method of claim 1, wherein:
the first component comprises elastomeric loop material forming a first layer of the material; and
the second component comprises foam forming a second layer of the material.

6. The method of claim 1, wherein the end stretch corresponds to an elongation in the range of 20 to 30 percent or in the range of 15 to 20 percent.

7. The method of claim 1, further comprising stretching, during the wrapping, the first band to the end stretch defined by the second component such that the first band is wrapped around the limb at or near end stretch.

8. The method of claim 1, wherein:
the therapeutic compression garment further comprises a plurality of bands, the first band being one of the plurality of bands; and
the wrapping further comprises varying an overlap among the plurality of bands to adjust the therapeutic compression delivered.

9. The method of claim 1, wherein the therapeutic compression garment further comprises a geometric figure attached to the first band, the geometric figure becoming a characteristic shape when the first band is stretched a proper amount.

10. The method of claim 9, wherein the proper amount is at or near the end stretch of the material.

11. The method of claim 9, wherein a color of the material or the geometric feature indicates the proper amount of stretch of the first band.

12. A method of treatment comprising:
obtaining a therapeutic compression garment comprising:
a first band of material, the material comprising a first, elastomeric component, a second component distinct from the first component, and the first component connected to the second component such that the second component limits the stretch of the first component to define an end stretch of the material, and
a first attachment mechanism connected to the first band;
wrapping the first band around a limb of a patient suffering from at least one of venous insufficiency, postphlebitic syndrome, lymphedema, edma, painful swelling, and excessive fluid accumulation;
securing, by the first attachment mechanism after the wrapping, the first band wrapped around the limb; and
delivering, by the therapeutic compression garment after the securing, therapeutic compression selected from the group consisting of 8-15 mm Hg, 15-20 mm Hg, 20-30 mm Hg, 30-40 mmHg, and greater than 40 mm Hg to the limb.

13. The method of claim 12, wherein the end stretch corresponds to an elongation in the range of 20 to 30 percent.

14. The method of claim 12, wherein the end stretch corresponds to an elongation in the range of 15 to 20 percent.

15. The method of claim 12, wherein the first component comprises a first layer of the material.

16. The method of claim 15, wherein the second component comprises a second layer of the material.

17. The method of claim 16, wherein the first layer overlays the second layer.

18. The method of claim 17, wherein the first layer comprises elastomeric loop material.

19. The method of claim 18, wherein the second layer comprises a woven elastomeric fabric.

20. The method of claim 18, wherein the second layer comprises foam.

21. The method of claim 16, wherein the material comprises a thin, semi-compressible layer positioned between the first layer and the second layer.

22. The method of claim 12, further comprising a geometric figure attached to the first band, the geometric figure becoming a characteristic shape when the first band is stretched a proper amount.

23. The method of claim 22, wherein the proper amount is at or near the end stretch of the material.

24. The method of claim 22, wherein a color of the material or the geometric feature indicates the proper amount of stretch of the first band.

25. The method of claim 12, wherein the material has an elastic stretch range of 15% to 100%.

26. A method of treatment comprising:
obtaining a therapeutic compression garment comprising:
a first band formed of a material,
a second band formed of the material,
the first and second bands, wherein the material comprises a first, elastomeric component, a second component, distinct from the first component, and the first component connected to the second component such that the second component limits the stretch of the first component to define an end stretch of the material,
a first attachment mechanism directly connected to the first band, and
a second attachment mechanism directly connected to the second band;
wrapping the first band around a limb of a patient suffering from at least one of venous insufficiency, postphlebitic syndrome, lymphedema, edma, painful swelling, and excessive fluid accumulation;
securing, by the first attachment mechanism after the wrapping the first band, the first band wrapped around the limb;
wrapping, after the securing the first band, the second band around the limb;
securing, by the second attachment mechanism after the wrapping the second band, the second band wrapped around the limb; and
delivering, by the therapeutic compression garment to the limb after the securing the first band and the securing the second band, therapeutic compression selected from the group consisting of 8-15 mm Hg, 15-20 mm Hg, 20-30 mm Hg, 30-40 mmHg, and greater than 40 mm Hg.

27. The method of claim 26, wherein the wrapping the second band comprises wrapping the second band so that the second band at least partially overlaps the first band.

28. The method of claim 26, wherein the compression garment further comprising a geometric figure attached to at least one of the first and second bands, the geometric figure becoming a characteristic shape when the at least one of the first and second bands is stretched a proper amount.

29. The method of claim 28, wherein the proper amount is at or near the end stretch of the material.

30. The method of claim 28, wherein a color of the material or the geometric feature indicates the proper amount of stretch of the at least one of the first and second bands.

31. The method of claim 26, wherein:
the first component comprises elastomeric loop material forming a first layer of the material; and
the second component comprises a woven elastomeric fabric forming a second layer of the material.

32. The method of claim 31, wherein the material further comprises a thin, semi-compressible layer positioned between the first layer and the second layer.

33. The method of claim 26, wherein:
the first component comprises elastomeric loop material forming a first layer of the material; and
the second component comprises foam forming a second layer of the material.

* * * * *